United States Patent
Osora et al.

(10) Patent No.: US 8,858,798 B2
(45) Date of Patent: *Oct. 14, 2014

(54) DEHYDRATION METHOD

(71) Applicant: Mitsubishi Heavy Industries, Ltd., Tokyo (JP)

(72) Inventors: Hiroyuki Osora, Hiroshima (JP); Yoshio Seiki, Hiroshima (JP); Atsuhiro Yukumoto, Hiroshima (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/053,161

(22) Filed: Oct. 14, 2013

(65) Prior Publication Data

US 2014/0051895 A1    Feb. 20, 2014

Related U.S. Application Data

(62) Division of application No. 12/743,997, filed as application No. PCT/JP2008/054777 on Mar. 14, 2008, now Pat. No. 8,585,904.

(30) Foreign Application Priority Data

Oct. 5, 2006    (JP) .................................. 2006-273918

(51) Int. Cl.
| | | |
|---|---|---|
| *B01D 15/00* | (2006.01) | |
| *B01D 3/00* | (2006.01) | |
| *C02F 1/44* | (2006.01) | |
| *C12C 11/00* | (2006.01) | |

(52) U.S. Cl.
USPC .............................. 210/640; 210/149; 203/10

(58) Field of Classification Search
CPC ............... B01D 61/362; B01D 53/228; B01D 2311/103; B01D 61/36; B01D 71/028; B01D 3/14; C02F 2103/08; B01J 20/28095
USPC ........... 210/640, 175, 500.25; 203/10, 18, 71; 202/154; 426/14
See application file for complete search history.

(56) References Cited

U.S. PATENT DOCUMENTS

| | | | |
|---|---|---|---|
| 3,608,610 A | | 9/1971 | Greatorex et al. |
| 4,895,989 A | * | 1/1990 | Sander et al. ................. 568/851 |

(Continued)

FOREIGN PATENT DOCUMENTS

| | | |
|---|---|---|
| GB | 2170219 A | 7/1986 |
| JP | 44-9443 B | 5/1969 |

(Continued)

OTHER PUBLICATIONS

Japanese Office Action dated Oct. 16, 2009, issued in Japanese Patent Application No. 2006-273918.
International Search Report of PCT/JP2008/054777, mailing date of Apr. 15, 2008.

(Continued)

*Primary Examiner* — Ana Fortuna
(74) *Attorney, Agent, or Firm* — Westerman, Hattori, Daniels & Adrian, LLP

(57) ABSTRACT

The present invention includes a dehydration method comprising the steps of providing a distilled process-target fluid to a water separation membrane device via a heat exchanger; separating the process-target fluid into a dehydrated product and water by using the water separation membrane device; detecting a temperature of any one of the water separation membrane device and the process-target fluid supplied to the water separation membrane device by using a temperature monitoring device; and controlling the temperature of the process-target fluid so that the temperature of the distilled process-target fluid being maintained at a temperature higher than the condensation temperature of the distillate by 5 to 10° C. by using a temperature adjustment device provided in the water separation membrane device.

4 Claims, 3 Drawing Sheets

(56) References Cited

U.S. PATENT DOCUMENTS

| | | | |
|---|---|---|---|
| 4,978,430 A * | 12/1990 | Nakagawa et al. | 203/14 |
| 4,997,462 A | 3/1991 | Nakatani et al. | |
| 5,105,029 A | 4/1992 | Ninomiya et al. | |
| 5,143,526 A | 9/1992 | Lee et al. | |
| 5,151,190 A | 9/1992 | Seiryo | |
| 5,294,345 A | 3/1994 | Kaschemekat | |
| 5,494,556 A | 2/1996 | Mita et al. | |
| 5,556,539 A | 9/1996 | Mita et al. | |
| 5,582,721 A | 12/1996 | Mita et al. | |
| 5,616,247 A | 4/1997 | Mita et al. | |
| 5,755,967 A | 5/1998 | Meagher et al. | |
| 5,868,906 A | 2/1999 | Adams et al. | |
| 6,210,464 B1 | 4/2001 | Nakanishi et al. | |
| 6,660,165 B1 | 12/2003 | Hirabayashi et al. | |
| 6,899,741 B2 | 5/2005 | Nakamura et al. | |
| 6,928,750 B2 | 8/2005 | Kashkoush et al. | |
| 7,045,062 B1 | 5/2006 | Aminabhavi et al. | |
| 7,459,084 B2 | 12/2008 | Baig et al. | |
| 7,655,141 B2 | 2/2010 | Bruschke et al. | |
| 7,699,961 B2 | 4/2010 | Ikeda et al. | |
| 7,732,173 B2 | 6/2010 | Mairal et al. | |
| 7,732,967 B2 | 6/2010 | Vollmer et al. | |
| 7,871,520 B2 | 1/2011 | Ma et al. | |
| 7,892,321 B2 | 2/2011 | Aagesen et al. | |
| 8,002,874 B2 | 8/2011 | Huang et al. | |
| 8,128,787 B2 | 3/2012 | Wynn et al. | |
| 8,142,662 B2 * | 3/2012 | Osora et al. | 210/640 |
| 2003/0101866 A1 | 6/2003 | Noack | |
| 2004/0000521 A1 | 1/2004 | Vane et al. | |
| 2004/0211726 A1 | 10/2004 | Baig et al. | |
| 2004/0256212 A1 | 12/2004 | Ikeda et al. | |
| 2007/0112189 A1 | 5/2007 | Ikeda et al. | |
| 2007/0284307 A1 | 12/2007 | Lin | |
| 2008/0099400 A1 | 5/2008 | Nemser et al. | |
| 2014/0014583 A1 | 1/2014 | Hanemaaijer | |

FOREIGN PATENT DOCUMENTS

| | | |
|---|---|---|
| JP | 50-132896 U | 10/1975 |
| JP | 54-33279 A | 3/1979 |
| JP | 58-11083 A | 1/1983 |
| JP | 58-021629 A | 2/1983 |
| JP | 60-202705 A | 10/1985 |
| JP | 62-11088 A | 1/1987 |
| JP | 62-237906 A | 10/1987 |
| JP | 63-278522 A | 11/1988 |
| JP | 01-236905 A | 9/1989 |
| JP | 2-71829 A | 3/1990 |
| JP | 02-229529 A | 9/1990 |
| JP | 2-273519 A | 11/1990 |
| JP | 2-059394 B2 | 12/1990 |
| JP | 04-281827 A | 10/1992 |
| JP | 4-313333 A | 11/1992 |
| JP | 5-103956 A | 4/1993 |
| JP | 06-254354 A | 9/1994 |
| JP | 6-277402 A | 10/1994 |
| JP | 6-287153 A | 10/1994 |
| JP | 06-304453 A | 11/1994 |
| JP | 7-124444 A | 5/1995 |
| JP | 9-220563 A | 8/1997 |
| JP | 10-180046 A | 7/1998 |
| JP | 11-156167 A | 6/1999 |
| JP | 2003-93828 A | 4/2003 |
| JP | 2003-530999 A | 10/2003 |
| JP | 2004-131024 A | 4/2004 |
| JP | 2004-255283 A | 9/2004 |
| JP | 2005-145773 A | 6/2005 |
| JP | 2007-045482 A | 2/2007 |
| JP | 2007-275690 A | 10/2007 |
| WO | 86/01425 A1 | 3/1986 |

OTHER PUBLICATIONS

International Search Report of PCT/JP2008/054782, mailing date of Apr. 22, 2008.
International Search Report of PCT/JP2008/054790, mailing date of Apr. 22, 2008.
Japanese Office Action dated Jul. 28, 2009, issued in Japanese Patent Application No. 2007-066287.
Japanese Office Action dated Nov. 17, 2009, issued in Japanese Patent Application No. 2007-066287.
International Search Report of PCT/JP2008/054791, mailing date of Apr. 8, 2008.
Japanese Office Action dated Jun. 24, 2011, issued in Japanese Patent Application No. 2007-066286.
European Search Report dated Dec. 5, 2011, issued in European Patent Application No. 08722178.4 (corresponding to U.S. Appl. No. 12/522,791).
European Search Report dated Dec. 5, 2011, issued in European Patent Application No. 08722186.7 (corresponding to U.S. Appl. No. 12/522,831).
European Search Report dated Dec. 5, 2011, issued in European Patent Application No. 08722187.5 (corresponding to U.S. Appl. No. 12/523,620).
Extended European Search Report dated Aug. 14, 2012, issued in European Patent Application No. 08722173.5 (6 pages).
U.S. Office Action dated Aug. 8, 2012, issued in technically related U.S. Appl. No. 12/743,997.
Related U.S. Appl. No. 12/523,620, filed Jul. 17, 2009.
Related U.S. Appl. No. 12/522,831, filed Jul. 10, 2009.
Japanese Office Action dated Jul. 28, 2009, issued in Japanese Patent Application No. 2007-305646.
U.S. Office Action dated Jul. 28, 2011, issued in U.S. Appl. No. 12/522,791.
U.S. Notice of Allowance dated Dec. 7, 2012, issued in U.S. Appl. No. 12/523,620.
U.S. Office Action dated Dec. 24, 2012, issued in corresponding U.S. Appl. No. 12/743,997.
Partial European Search Report dated Sep. 28, 2012, issued in European Patent Application No. 12175826.2 (corresponding to U.S. Appl. No. 12/522,791) (8 pages).
Extended European Search Report dated Feb. 11, 2013, issued in European Patent Application No. 12175826.2 (corresponding to U.S. Appl. No. 12/522,791).
Canadian Office Action dated Jan. 4, 2013, issued in Canadian Patent Application No. 2,706,047 (corresponding to U.S. Appl. No. 12/743,997).
Canadian Notice of Allowance dated Jan. 23, 2013, issued in Canadian Patent Application No. 2,675,399 (corresponding to U.S. Appl. No. 12/522,831).
Canadian Notice of Allowance dated Mar. 8, 2013, issued in Canadian Patent Application No. 2,676,899 (corresponding to U.S. Appl. No. 12/523,620) (1 page).
Examiner's Answer dated Feb. 24, 2013, issued in U.S. Appl. No. 12/522,831.
U.S. Notice of Allowance dated Apr. 3, 2013, issued in U.S. Appl. No. 12/523,620.
US Office Action dated Apr. 2, 2013, issued in U.S. Appl. No. 12/743,997 (21 pages).
Canadian Notice of Allowance dated Jul. 9, 2013, issued in Canadian Patent Application No. 2,706,047 (1 page).
European Notice of Allowance dated Jul. 23, 2013, issued in European Patent Application No. 08 722 173.5 (27 pages).
U.S. Office Action dated Jul. 23, 2013, issued in U.S. Appl. No. 12/522,791 (29 pages).
U.S. Office Action dated Apr. 15, 2014, issued in U.S. Appl. No. 12/522,791 (9 pages).
Non-Final Office Action issued Aug. 22, 2014 in related U.S. Appl. No. 12/522,831 (29 pages).

* cited by examiner

DEHYDRATION METHOD

CROSS-REFERENCE TO RELATED APPLICATIONS

The present application is a divisional of U.S. patent application Ser. No. 12/743,997, filed May 20, 2010, which is a U.S. National Stage entry of International Application No. PCT/JP2008/054777, filed Mar. 14, 2008, the entire contents of which are incorporated herein by reference.

TECHNICAL FIELD

The present invention relates to a dehydration system and a dehydration method. More specifically, the present invention relates to a dehydration system and a dehydration method for efficiently dehydrating a mixture (process-target fluid) of water and ethanol or propanol forming an azeotropic composition with water.

BACKGROUND ART

Ethanol is receiving attention as a fuel source substituting for an oil fuel. The market size of ethanol is predicted to be 55 million kilo litters in 2010. Adoption of methanol as a fuel, however, requires distillation of a crude product obtained from a biomass such as corn, and then dehydration of the resultant product to obtain at least 99.5 wt % or more.

What has conventionally practiced for such dehydration is to: distill and concentrate a dilute ethanol aqueous solution in a distillation tower until ethanol/water azeotropic point is nearly reached; and then dehydrate the distillate.

One of dehydration methods involves addition of an entrainer and dehydration through azeotropic distillation. This method, however, requires processes such as the azeotropic distillation of three-component system and recovery of the entrainer, and therefore has several drawbacks such as needing an enormous amount of heat energy.

In another one of dehydration methods, multiple molecular sieve vessels are arranged in parallel, and dehydration is performed by switching the molecular sieve vessels on a batch basis. This method too, however, has a drawback of consuming an enormous amount of energy to recover the molecular sieve vessels.

Then, it is conceivable to use an element, such as a separation membrane, that does not bring the above drawbacks (Patent Literature 1: JP 58-21629 A). A method using such separation membrane, however, is actually impractical because too much cost is required for a water separation membrane for large-scale dehydration.

[Patent Literature 1] JP58-21629 A

DISCLOSURE OF THE INVENTION

Problem to be Solved by the Invention

The present invention has been made in consideration of the above circumstances, and has an objective to provide a dehydration system and a dehydration method in which an amount of water permeation per a membrane area of a water separation membrane is increased to thereby improve separation performances of the membrane.

Means for Solving the Problem

To attain the above objective, the present invention provides a dehydration system that includes: a water separation membrane device that separates a process-target fluid into an anhydride and water; and a temperature monitoring device for any one of the water separation membrane device and the process-target fluid supplied to the water separation membrane device. In the dehydration system, the temperature monitoring device detects a temperature, and a temperature adjustment device is provided in a previous stage of the water separation membrane device. The temperature adjustment device controls a temperature of the process-target fluid on the basis of the temperature detected by the temperature adjustment device to thereby optimize an amount of water permeation in a separation process in the water separation membrane device.

The process-target fluid intended by the dehydration system according to the present invention is generally a mixture of ethanol and water or a mixture of propanol and water.

In a preferred embodiment of the dehydration system according to the present invention, the process-target fluid is a gaseous or liquid distillate obtained by distilling a raw material in a distillation tower.

In addition, in another mode of the dehydration system according to the present invention, the process-target fluid is obtained by dehydrating a raw material through an alcohol selective permeation film.

Moreover, in still another mode of the dehydration system according to the present invention, moisture obtained by the water separation membrane device is reused in a device for obtaining the process-target fluid.

Preferably, the water separation membrane is an inorganic, silica- or zeolite-based water separation membrane having a pore size of 10 angstroms or less.

Furthermore, in yet another mode of the dehydration system according to the present invention, the dehydration system further includes: a cooling device and a gas-liquid separation device for cooling moisture obtained by the water separation membrane device and for separating the moisture into a gas and a liquid.

Another aspect of the present invention is a dehydration method using the dehydration system according to the present invention. In the dehydration method, a water separation membrane device separates a process-target fluid into an anhydride and water, and a temperature monitoring device detects a temperature of any one of the water separation membrane device and the process-target fluid supplied to the water separation membrane device. A temperature adjustment device controls the temperature of the process-target fluid on the basis of the temperature detected by the temperature adjustment device to thereby optimize an amount of water permeation in a separation process in the water separation membrane device, the temperature adjustment device being provided in a previous stage of the water separation film device.

Effects of the Invention

The present invention provides a dehydration system and a dehydration method in which an amount of water permeation per a membrane area of a water separation membrane is increased to thereby improve separation performances of the membrane.

Figure 1:
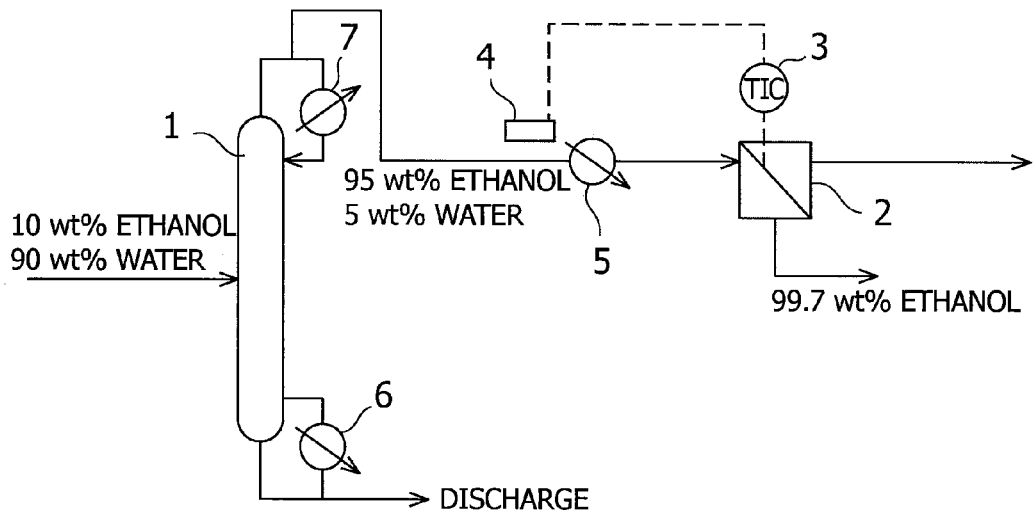
FIG. 1 is a schematic diagram illustrating an embodiment of a dehydration system according to the present invention.

EXPLANATION OF REFERENCE NUMERALS 1 distillation tower
2 water separation membrane device
3 temperature measurement device
4 heat-medium flow rate controller
5 heat exchanger
6 heat exchanger
7 heat exchanger
31 line
51 line
61 line
62 cooler
63 gas-liquid separator
64 circulating pump

BEST MODES FOR CARRYING OUT THE INVENTION

A dehydration system and a dehydration method according to the present invention will be described below in further detail by referring to embodiments thereof.

FIG. 1 shows an embodiment of a dehydration system according to the present invention. The dehydration system according to the embodiment assumes that a dilute ethanol aqueous solution is used as a raw material supplied to a distillation tower. The dilute ethanol aqueous solution generally refers to an aqueous solution having an ethanol concentration of 8 wt % to 15 wt %. Note that an aqueous solution having a 10 wt % ethanol is assumed in the embodiment in FIG. 1. This is also true to embodiments in FIGS. 3 to 6.

As main constituents, the dehydration system includes a distillation tower 1, a water separation membrane device 2, a temperature measurement device 3, and a heat-medium flow rate controller 4.

The distillation tower 1 is of a type that is supplied with steam at a bottom portion thereof, heats a dilute ethanol aqueous solution supplied to a middle portion thereof, and distills a concentrated raw material from a top of the tower. The distillate is a mixture of ethanol and water, the ethanol concentration of which has become higher.

The water separation membrane device 2 is a device for separating the distillate (process-target fluid) into absolute ethanol (99.5 wt % or more ethanol) and water. A water separation membrane constituting the water separation membrane device is preferably an inorganic, silica- or zeolite-based water separation membrane having a pore size of 10 angstroms or less.

Alternatively, an inorganic water separation membrane described in U.S. Pat. No. 2,808,479 can be used. The inorganic water separation membrane of U.S. Pat. No. 2,808,479 is an acid-resistant compound separation membrane obtained by supporting silica gel in pores of an inorganic porous body, the silica gel being obtained through hydrolysis of alkoxysilane including ethoxy or methoxy. The acid-resistant compound separation membrane can be manufactured by a manufacturing method including Steps 1 to 11 given below.

Step 1: In conditions for preparing multiple types of silica sol which are fabricated by changing the mixture ratio of raw materials of the silica sol, namely, alkoxysilane, water, and an acid catalyst, the blending ratio of the raw materials of the silica sol to be supported is divided into two types: one for a silica sol 1 and one for a silica sol 2.

Step 2: For the raw materials for the silica sol 1, the weight ratio of water to alkoxysilane is set to 0.5 to 2.0, and the weight ratio of the acid catalyst to alkoxysilane is set to 0.01 to 0.1 as a reaction catalyst.

Step 3: For the raw materials for the silica sol 2, the weight ratio of water to alkoxysilane is set to 2.0 to 50, and the weight ratio of the acid catalyst to alkoxysilane is set to 0.01 to 0.5 as a reaction catalyst.

Step 4: The raw materials for the silica sol 1 is kept boiling, and a fluid obtained after about 25-minute boiling, a fluid obtained after about 20-minute boiling, and a fluid obtained after about 15-minute boiling are set as a fluid 1-A, a fluid 1-B, and a fluid 1-C, respectively.

Step 5: The silica sol 2 is fabricated by stirring and mixing the raw materials for the silica sol 2 for 30 minutes to 90 minutes at a room temperature.

Step 6: The above silica sol fluid 1-A is supported on a surface of a porous base. Thereafter, the porous base is calcined for 5 to 15 minutes in an electric furnace set at about 200° C. Next, the porous body is calcined for 5 to 15 minutes in an electric furnace set at about 300° C. Next, the porous base is calcined for 5 to 15 minutes in an electric furnace set at about 400° C. Next, the porous base is calcined for 5 to 15 minutes in an electric furnace set at about 500° C.

Step 7: The silica sol fluid 1-A is again supported on the surface of the porous base in which the above silica sol fluid 1-A is supported. Thereafter, the process in Step 6 described above is repeated two or three times.

Step 8: Next, using the silica sol fluid 1-B, processes similar to those of Steps 6 and 7 described above are performed on the surface of the porous base in which the above silica sol fluid 1-A is supported.

Step 9: Next, using the silica sol fluid 1-C, processes similar to those of Steps 6 and 7 described above are performed on the surface of the porous base in which the above silica sol fluid 1-B is supported.

Step 10: Next, the silica sol fluid 2 is supported on the surface of the porous base in which the silica sol fluids 1-A, 1-B, and 1-C are supported. Then, the porous body is calcined for 5 to 15 minutes in an electric furnace set at about 200° C. Next, the porous base is calcined for 5 to 15 minutes in an electric furnace set at about 300° C. Next, the porous base is calcined for 5 to 15 minutes in an electric furnace set at about 400° C. Next, the porous base is calcined for 5 to 15 minutes in an electric furnace set at about 500° C.

Step 11: the silica sol fluid 2 is again supported on the surface of the porous base in which the above silica sol fluid 2 is supported. Thereafter, the process in Step 10 described above is repeated two or three times.

The temperature measurement device 3 is a device for measuring the temperature of a distillate, and constitutes a temperature monitoring device. Generally, an electric heat sensor such as a thermocouple, or a temperature sensor such as a bimetallic thermometer is used. Such temperature sensor is mounted on a water separation membrane to measure the temperature of the water separation membrane per se, thereby measuring the temperature of the distillate. Note that the temperature of the distillate per se can be alternatively measured.

The heat-medium flow rate controller 4 constitutes a temperature adjustment device. As will be described later, the heat-medium flow rate controller 4 controls the amount of flow of a heat medium flowing into a heat exchanger 5, and thereby controls the temperature of a distillate supplied to the water separation membrane device 2.

Next, a description is given of an embodiment of a method of dehydrating a distillate by using the dehydration system according to the above embodiment.

As FIG. 1 shows, a mixture (raw material mixture) of 10-wt % ethanol and 90-wt % water is supplied to the middle portion of the distillation tower 1. In the meantime, the bottom portion of the distillation tower 1 is heated.

By a distillation process in the distillation tower 1, a mixture (process-target fluid) of 95-wt % ethanol and 5-wt % water is distilled from the top of the tower. Water is discharged from the bottom portion. Part of the discharged water undergoes heat exchange in a heat exchanger 6. Part of the distillate distilled from the top of the tower branches off to a heat exchanger 7, is liquefied again, and returns to the top of the tower. The other part of the distillate is fed to the water separation membrane device 2 through the heat exchanger 5.

The water separation membrane device 2 separates water from the distillate. What is generally performed here is to, with a negative pressure, collect water vapor generated from one of the sides of the water separation membrane.

Here, in the dehydration system according to the present invention, the temperature measurement device 3 detects the temperature of the water separation membrane. The temperature detection can be performed by detecting the temperature of the distillate per se or the temperature of the water separation film.

The detected temperature is passed to the heat-medium flow rate controller 4. The heat-medium flow rate controller 4 controls the temperature of the distillate by using the heat medium fed to the heat exchanger 5. To be more specific, the heat-medium flow rate controller 4 controls the amount of flow of the heat medium into the heat exchanger 5 so that the temperature of the gaseous distillate may be maintained at a temperature higher than the condensation temperature of the distillate by 5 to 10° C. Such temperature detection and heat-medium flow amount control based thereon can be performed using a technique known to those skilled in the art. In the embodiment, the distillation supplied from the distillation tower 1 in a gas form is about 80° C., and is then controlled to be in an about 90° C. range. In other words, the distillation is controlled to have a temperature higher than the condensation temperature thereof by 5 to 10° C. This increases the amount of water permeation per a membrane area of the water separation membrane, and thus improves the separation performances of the membrane.

Figure 2:
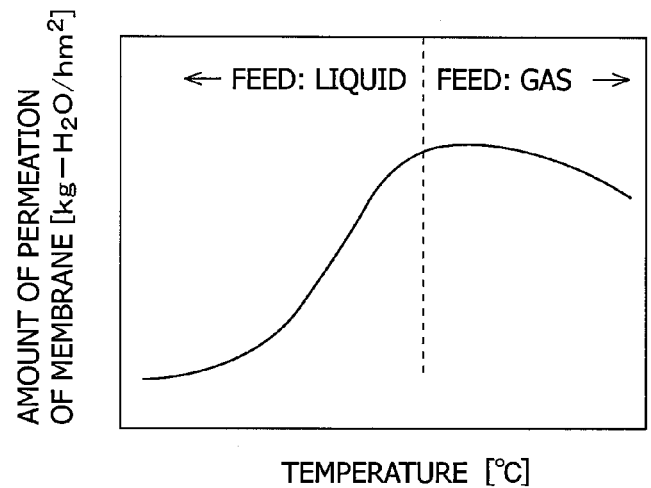
FIG. 2 is a graph showing relationships between an amount of water permeation and a temperature in a water separation membrane.

The temperature of the gaseous distillate is maintained here at a temperature higher than the condensation temperature of the distillate by 5 to 10° C. because such temperature allows a maximum dehydration efficiency to be obtained, as shown in FIG. 2.

By a dehydration process of the water separation membrane device 2, absolute ethanol (having an ethanol concentration of 99.5 wt % or higher) is collected.

Figure 3:
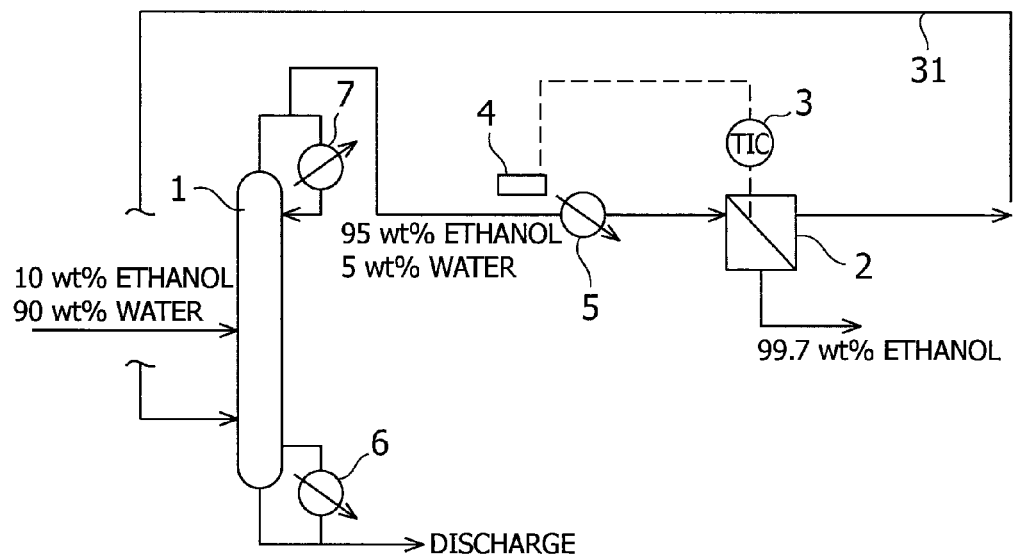
FIG. 3 is a schematic diagram illustrating another embodiment of a dehydration system according to the present invention.

Next, FIG. 3 shows another embodiment of a dehydration system according to the present invention.

In this embodiment, a line 31 is provided so that moisture obtained by the water separation membrane device 2 can be recycled, remaining in a gas form. It can be expected thereby to collect a small amount of ethanol that has undesirably permeated through the water separation membrane. Note that the other constituents are the same as those described in the embodiment described with FIG. 1, and that constituents denoted with the same number have the same configuration and action.

Figure 4:
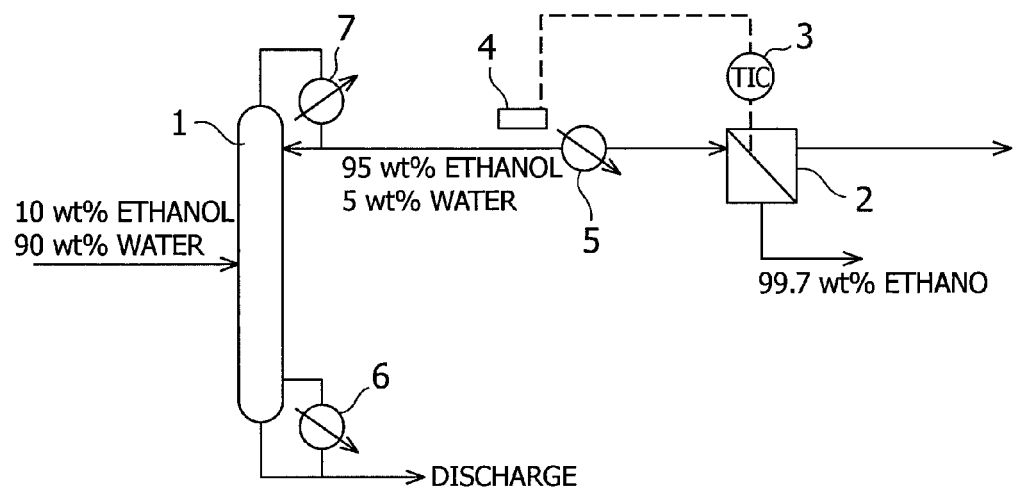
FIG. 4 is a schematic diagram illustrating another embodiment of a dehydration system according to the present invention.

Next, FIG. 4 shows still another embodiment of a dehydration system according to the present invention.

In this embodiment, a gaseous distillate obtained by the distillation tower 1 is liquefied in the heat exchanger 7 which then returns part of the distillate to the distillation tower 1 and feeds the other part of the liquid distillate to the water separation membrane device 2 side.

In this embodiment, the liquid distillate is heated in the heat exchanger 5. In this embodiment, the distillate supplied from the distillation tower 1 in a liquid form is about 40° C., and is then gasified and controlled to be in an about 90° C. range. In other words, the distillate is controlled to have a temperature higher than the condensation temperature thereof by 5 to 10° C. This increases the amount of water permeation per a membrane area of the water separation membrane, and thus improves the separation performances of the membrane.

The reason why the temperature of the gaseous distillate is maintained here at a temperature higher than the condensation temperature thereof by 5 to 10° C. is based on the reason described using FIG. 2 in the embodiment in FIG. 1.

Note that the other constituents are the same as those described in the embodiment described with FIG. 1, and that constituents denoted with the same number have the same configuration and action.

Figure 5:
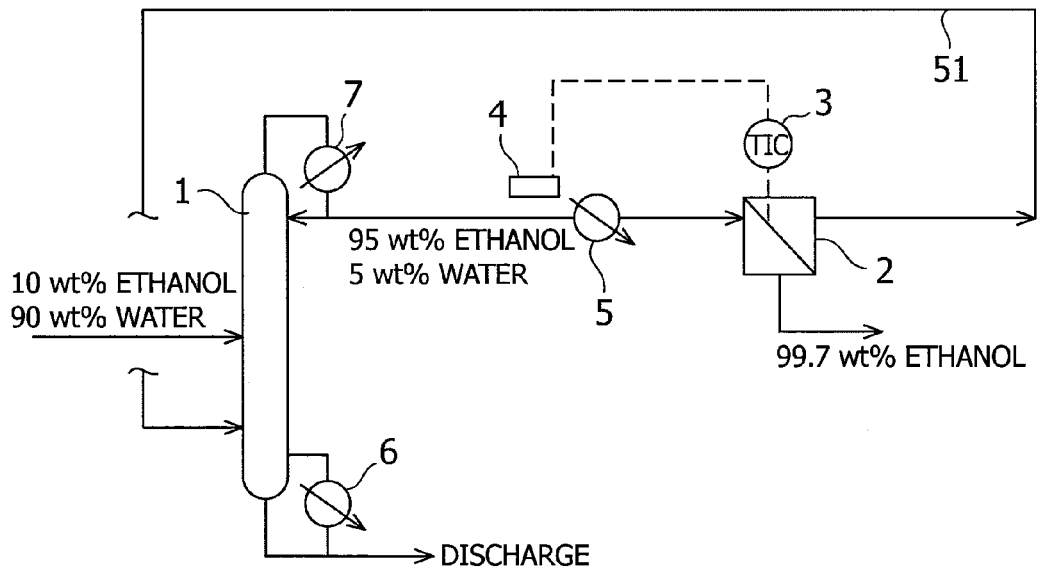
FIG. 5 is a schematic diagram illustrating another embodiment of a dehydration system according to the present invention.

Next, FIG. 5 shows yet another embodiment of a dehydration system according to the present invention.

In this embodiment, a line 51 is provided so that moisture obtained by the water separation membrane device 2 can be recycled, remaining in a gas form. It can be expected thereby to collect a small amount of ethanol gas that has undesirably permeated through the water separation membrane. Note that the other constituents are the same as those described in the embodiment described with FIG. 4, and that constituents denoted with the same number have the same configuration and action.

Figure 6:
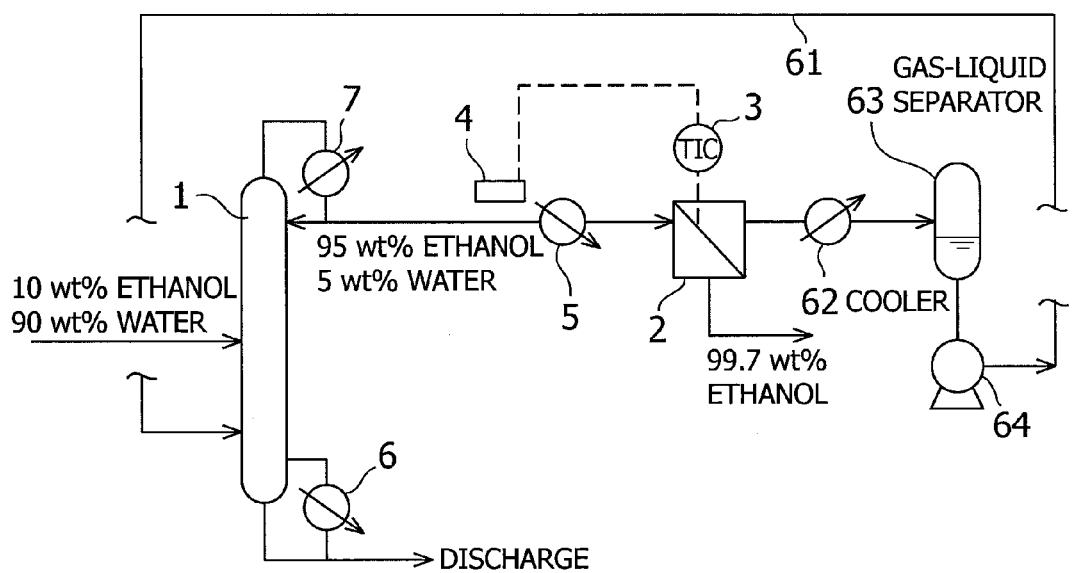
FIG. 6 is a schematic diagram illustrating another embodiment of a dehydration system according to the present invention.

Next, FIG. 6 shows still another embodiment of a dehydration system according to the present invention.

In this embodiment, moisture, which is returned to the distillation tower 1 in a gas form in the embodiment in FIG. 5, is supplied in a liquid form.

Specifically, in this embodiment, a cooler 62, a gas-liquid separator 63, and a circulating pump 64 are included in addition to those of the embodiment in FIG. 5. The cooler 62 cools a gas (water vapor) from the water separation membrane device 2, and the gas-liquid separator 63 separates out water (liquid). The circulating pump 64 returns the water to the distillation tower 1 through a line 61. It can be expected thereby to collect, in a liquid form, a small amount of ethanol gas that has undesirably permeated through the water separation membrane.

Note that, like this embodiment, the embodiment in FIG. 3 can also be implemented as a mode that further includes the cooler 62, the gas-liquid separator 63, and the circulating pump 64.

In the embodiments in FIG. 1 and FIGS. 3 to 6, a gaseous distillate is supplied to the water separation membrane device 2. Alternatively, a liquid distillate may be supplied. Also in this case, the temperature of the distillate is controlled to be as far to the high side as possible. This increases the amount of water permeation per a membrane area of the water separation membrane, and thus improves the separation performances of the membrane.

In the embodiments in FIG. 1 and FIGS. 3 to 6, a dilute ethanol aqueous solution is processed in the distillation tower 1. In such a case where a dilute ethanol aqueous solution is processed in the distillation tower 1, the distillate should preferably have an ethanol concentration (alcohol concentration) of 80 to 95 wt %.

Moreover, in place of the distillation tower, a device employing an alcohol selective membrane may be used. An example of such alcohol selective membrane is an ethanol selective permeation film formed of a high polymer film made of silicon rubber or trimethylsilyl propyne.

In such a case where a dilute ethanol aqueous solution is processed using the alcohol selective film, a process-target material should preferably have an ethanol concentration (alcohol concentration) of 50 to 95 wt %.

The invention claimed is:

1. A dehydration method comprising the steps of:
   providing a distilled process-target fluid to a water separation membrane device via a heat exchanger, the process-target fluid consisting of a mixture comprising ethanol and water or a mixture comprising propanol and water;
   separating the process-target fluid into a dehydrated product and water by using the water separation membrane device;
   detecting a temperature of any one of the water separation membrane device and the process-target fluid supplied to the water separation membrane device by using a temperature monitoring device provided on the membrane; and
   controlling the temperature of the process-target fluid so that the temperature of the distilled process-target fluid being maintained at a temperature higher than the condensation temperature of the distillate by 5 to 10° C. by using a temperature adjustment device provided in the water separation membrane device, the temperature adjustment device is a heat-medium flow rate controller which controls the amount of the heat medium into the heat exchanger on the basis of the temperature detected by the temperature monitoring device to optimize an amount of water permeation in a separation process in the water separation membrane device, wherein
   the process-target fluid is a gaseous distillate or a liquid distillate obtained by distilling a raw material in a distillation tower,
   and
   the distillation tower has a structure, where steam is supplied at a bottom portion, the raw material supplied to a middle portion is heated, and a concentrated raw material is distilled from a top portion of the distillation tower.

2. The dehydration method according to claim 1, wherein moisture obtained by the water separation membrane device is reused in the distillation tower.

3. The dehydration method according to claim 2, further comprising a cooling device and a gas-liquid separation device for cooling moisture obtained by the water separation membrane device and for separating the moisture into a gas and a liquid, wherein
   the moisture is obtained as a permeate from the water separation membrane.

4. The dehydration method according to claim 1, wherein the water separation membrane is an inorganic, silica- or zeolite-based water separation membrane having a pore size of 10 angstroms or less and water vapor permeable.

* * * * *